(12) United States Patent
Shirahata et al.

(10) Patent No.: US 7,750,308 B2
(45) Date of Patent: Jul. 6, 2010

(54) COMPTON CAMERA DEVICE

(75) Inventors: Takashi Shirahata, Tokyo (JP); Ryota Kohara, Tokyo (JP); Tetsuo Nakazawa, Tokyo (JP); Osamu Miyazaki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 9 days.

(21) Appl. No.: 12/304,284

(22) PCT Filed: Jun. 11, 2007

(86) PCT No.: PCT/JP2007/061695

§ 371 (c)(1),
(2), (4) Date: Dec. 11, 2008

(87) PCT Pub. No.: WO2007/145154

PCT Pub. Date: Dec. 21, 2007

(65) Prior Publication Data
US 2009/0202041 A1 Aug. 13, 2009

(30) Foreign Application Priority Data
Jun. 14, 2006 (JP) ............................. 2006-164527
Oct. 2, 2006 (JP) ............................. 2006-270222

(51) Int. Cl.
*G01T 1/20* (2006.01)
(52) U.S. Cl. .............................................. 250/370.09
(58) Field of Classification Search ............ 250/370.09; 378/86
See application file for complete search history.

(56) References Cited

U.S. PATENT DOCUMENTS

| | | | |
|---|---|---|---|
| 6,323,492 B1 * | 11/2001 | Clinthorne | 250/394 |
| 6,484,051 B1 * | 11/2002 | Daniel | 600/436 |
| 2002/0008205 A1 * | 1/2002 | Kurfess et al. | 250/370.13 |
| 2004/0251418 A1 * | 12/2004 | Gunter | 250/369 |
| 2005/0023474 A1 * | 2/2005 | Persyk et al. | 250/370.1 |
| 2005/0211909 A1 * | 9/2005 | Smith | 250/393 |

FOREIGN PATENT DOCUMENTS

| | | |
|---|---|---|
| JP | 06-201832 | 7/1994 |
| JP | 09-159767 | 6/1997 |
| JP | 2002-357661 | 12/2002 |

* cited by examiner

*Primary Examiner*—David P Porta
*Assistant Examiner*—Marcus H Taningco
(74) *Attorney, Agent, or Firm*—Antonelli, Terry, Stout & Kraus, LLP.

(57) ABSTRACT

A Compton camera device according to the invention includes first means for reading coordinate data of a scattering point of a quantum ray detected by a pre-stage detector for each Compton scattering event, second means for reading coordinate data of a reaching point of the Compton-scattered quantum ray detected by a post-stage detector for each Compton scattering event, and third means for calculating a measurement accuracy of the scattered quantum ray by the first and second means for each Compton scattering event, calculating a statistical quantity of the quantum ray for each calculated measurement accuracy, and outputting the calculated statistical quantity to image reconstruction means.

10 Claims, 9 Drawing Sheets

COMPTON CAMERA DEVICE

TECHNICAL FIELD

The present invention relates to a Compton camera device for measuring Compton scattering of a quantum ray including a cosmic ray and a gamma ray and imaging the distribution of the measured quantum ray, and more particularly, to a Compton camera device employing an imaging technique considering the measurement accuracy of the quantum ray.

BACKGROUND ART

In the past, Compton cameras using Compton scattering have imaged a quantum ray by a Compton method (for example, Patent Document 1).

Patent Document 1: JP-A-2002-357661

DISCLOSURE OF THE INVENTION

Problem that the Invention is to Solve

However, in the case of the conventional technique, the Compton scattering event which is high in measurement accuracy of the quantum ray and the Compton scattering event which is low in measurement accuracy are treated as the same events, and thus consideration on an effect of the difference in measurement accuracy on a reconstructed image has remained as an unsolved problem.

An object of the invention is to provide a Compton camera device capable of obtaining a reconstructed image which is not affected by the difference in measurement accuracy.

Means for Solving the Problem

In order to achieve the object, a Compton camera device according to the invention includes a pre-stage detector (51) for directly detecting a quantum ray including a cosmic ray and a gamma ray, a post-stage detector (52) for detecting the quantum ray incident to the pre-stage detector (51) and scattered by a Compton scattering phenomenon, image reconstruction means (56) for reconstructing the distribution of the quantum ray detected by the pre-stage detector (51) and the post-stage detector (52) as image information, and display means (57) for displaying the image information subjected to the image reconstruction. The device further includes first means (53) for reading coordinate data of a scattering point of the quantum ray detected by the pre-stage detector (51) for each Compton scattering event, second means (54) for reading coordinate data of a reaching point of the Compton-scattered quantum ray detected by the post-stage detector (52) for each Compton scattering event, and third means (55) for calculating a measurement accuracy of the scattered quantum ray by the first and second means (53 and 54) for each Compton scattering event, calculating a statistical quantity of the quantum ray for each calculated measurement accuracy, and outputting the calculated statistical quantity to the image reconstruction means (56).

Advantage of the Invention

According to the invention, a Compton camera device capable of obtaining a reconstructed image which is not affected by the difference in measurement accuracy can be provided.

DESCRIPTION OF REFERENCE NUMERALS AND SIGNS

51: PRE-STAGE DETECTOR
52: POST-STAGE DETECTOR
53: PRE-STAGE DATA READER
54: POST-STAGE DATA READER
55: DATA INTEGRATION DEVICE
56: IMAGE RECONSTRUCTION DEVICE
57: DISPLAY DEVICE
58: INPUT DEVICE
59: STORAGE DEVICE

BEST MODE FOR CARRYING OUT THE INVENTION

An embodiment of the invention will be described using the drawings.

Figure 1:
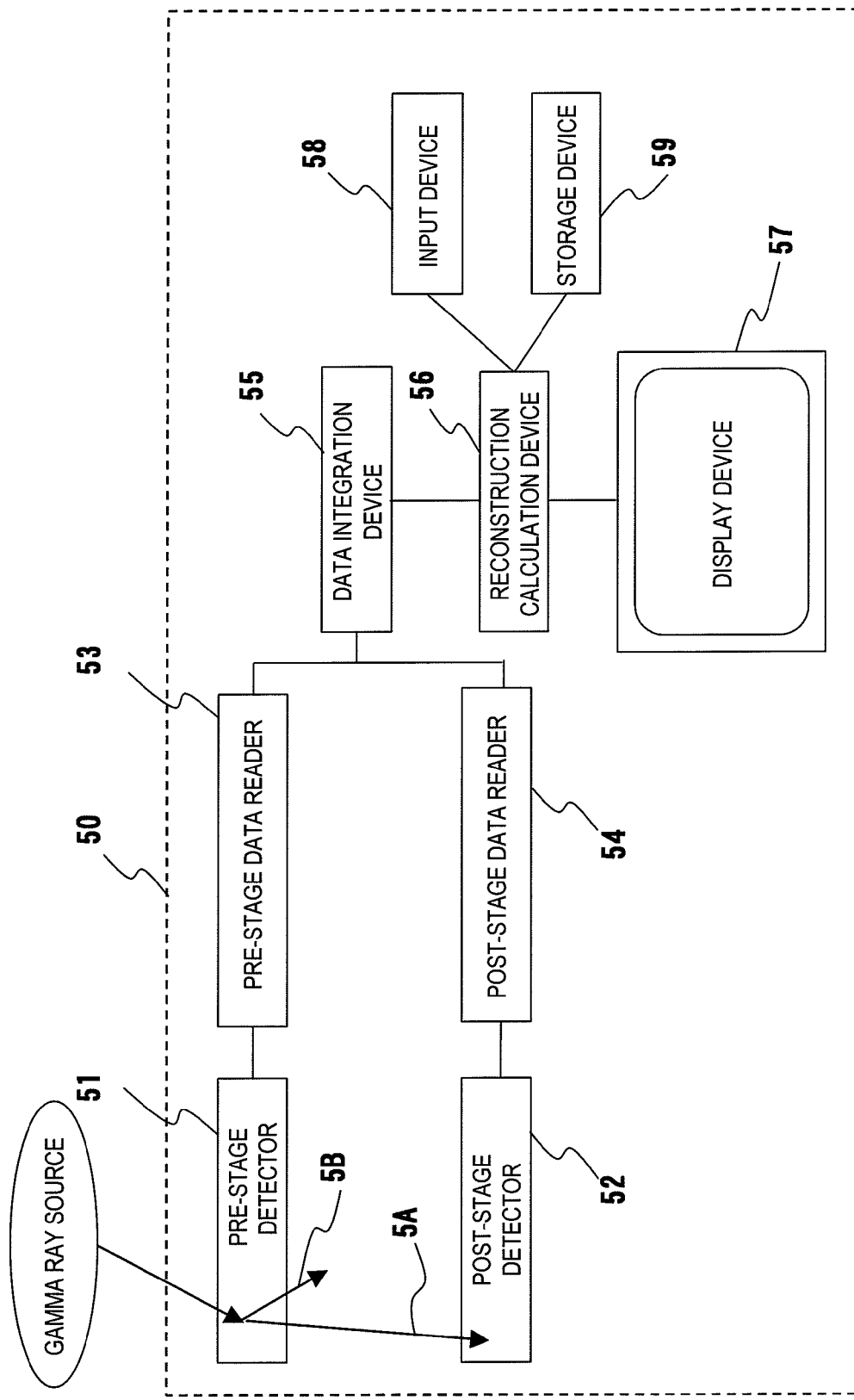
FIG. 1 is a diagram showing an example of a Compton camera system according to the invention.

FIG. 1 shows an example of a Compton camera system according to the invention. Since a gamma ray is used as a quantum ray in this description, the Compton camera system is also referred to as the gamma camera system. The gamma camera system has components having the following functions. A pre-stage detector 51 is disposed near a gamma ray source to cause Compton scattering and generate a scattered gamma ray and a recoil electron.

A post-stage detector 52 detects the scattered gamma ray. A pre-stage data reader 53 is connected to the pre-stage detector 51 to read physical quantities such as a recoil electron energy and a Compton scattering reaction point coordinate detected by the pre-stage detector 51. A post-stage data reader 54 is connected to the post-stage detector 52 to read physical quantities such as a scattered gamma ray energy and a scattered gamma ray absorbing position coordinate detected by the post-stage detector 52. A data integration device 55 is connected to the pre-stage data reader 53 and the post-stage data reader 54 to integrate the data thereof and newly calculate physical quantities such as a Compton scattering angle and a direction of the scattered gamma ray. An image reconstruction device 56 is connected to the data integration device 55 to acquire information such as the scattering angle and the coordinate of the Compton scattering reaction point from the data integration device 55 and perform image reconstruction calculation of the ray source. A display device 57 displays the information subjected to the reconstruction calculation as an image.

An input device 58 is used to input reconstruction calculation conditions to the image reconstruction device 56. Specifically, the input device is a keyboard or a mouse. A storage device 59 is used to store pre-set reconstruction calculation conditions, measurement error information of the evaluated camera and the like, and if necessary, provides them to a reconstruction calculation device.

Figure 2:
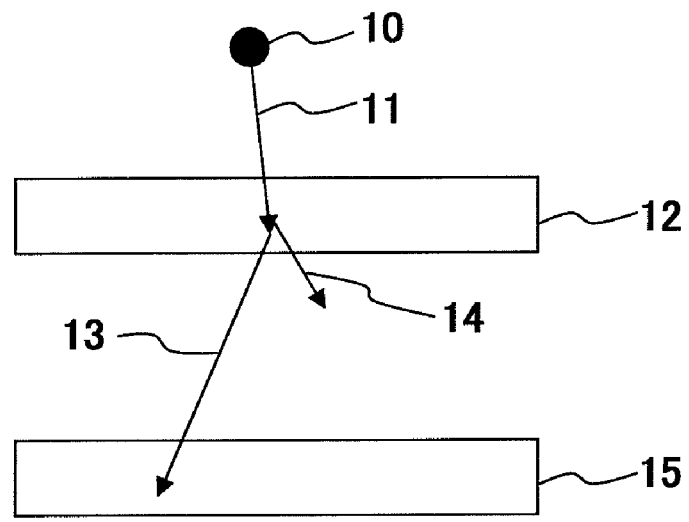
FIG. 2 is an explanatory diagram of an example of the Compton camera.

The outline of a Compton camera is shown in FIG. 2. The Compton camera includes two pre- and post-stage detectors. A gamma ray 11 generated from a gamma ray source 10 (hereinafter, referred to as "ray source") is Compton-scattered by a pre-stage detector 12 and a scattered gamma ray 13 and a recoil electron 14 are irradiated from the pre-stage detector 12.

Next, a post-stage detector 15 detects the scattered gamma ray 13. The pre-stage detector 12 detects as a Compton scattering position C (x, y, z) the coordinate at which the Compton scattering is caused. The cosine of a scattering angle φ can be calculated using (Formula 1) from a recoil electron energy Ee detected by the pre-stage detector 12 and a scattered gamma ray energy Eγ detected by the post-stage detector 15.

{Expression 1}

$$\cos\phi = 1 - \left(\frac{m_e c^2}{E_y} - \frac{m_e c^2}{E_e + E_y}\right) \quad \text{(Formula 1)}$$

Where $m_e c^2$ is a static energy of the electron.

Figure 3:
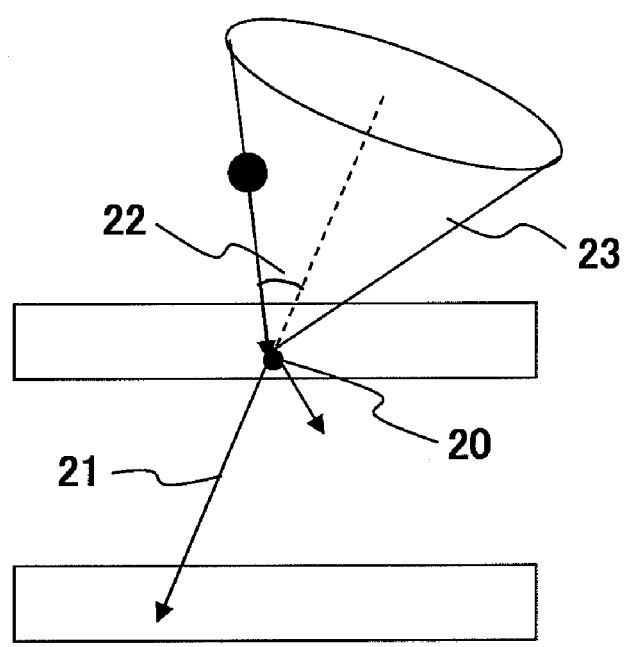
FIG. 3 is an explanatory diagram of a Compton method not considering a measurement error.
Figure 4:
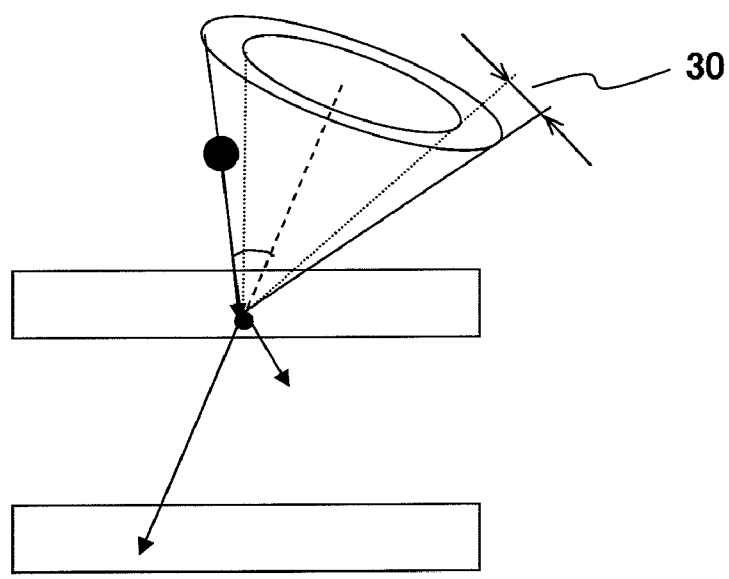
FIG. 4 is an explanatory diagram of the Compton method considering the measurement error.
Figure 5:
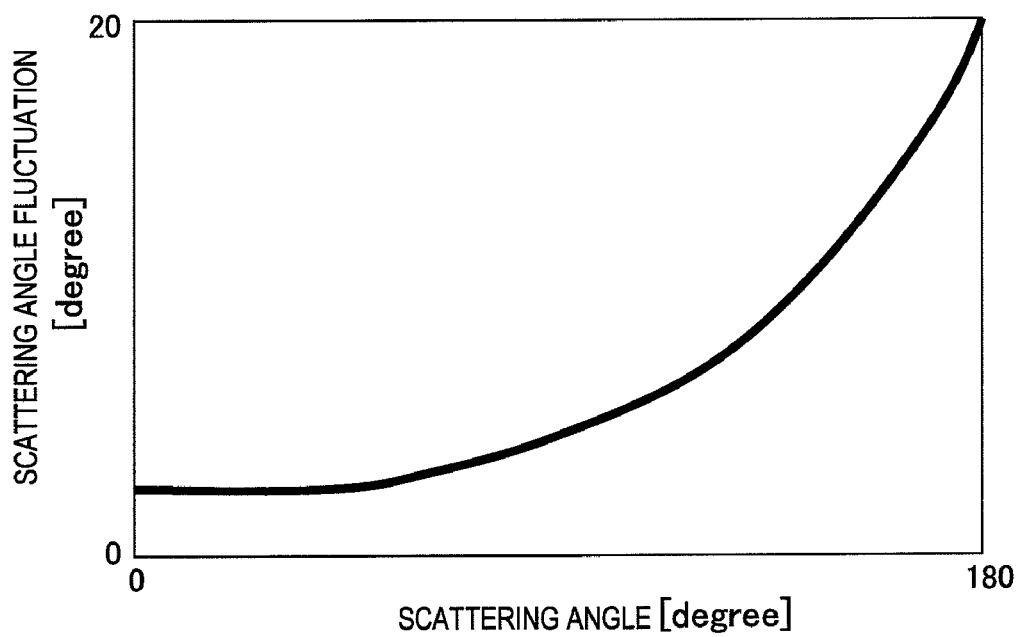
FIG. 5 is a relationship diagram of a scattering angle and a scattering angle fluctuation quantity.

As shown in FIG. 3, from the Compton scattering phenomenon, a Compton scattering position 20, a scattered gamma ray direction 21, a Compton scattering angle 22, a gamma ray generation position which is somewhere on a surface of a cone 23 (hereinafter, referred to as "Compton scattering cone") are obtained. Herein, the measurement error resulting from energy resolution of the detectors is considered. As shown in FIG. 4, the measurement error is represented by a thickness 30 of the surface of the Compton scattering cone. Hereinafter, the thickness is referred to as the scattering angle fluctuation. As shown in FIG. 5, in a Compton method, the scattering angle fluctuation 30 is used as an average measurement error of the whole Compton scattering events.

The gamma ray source is imaged by obtaining a Compton scattering cone for each Compton scattering event with reference to the measurement error and superposing the Compton scattering cones.

Embodiments of the invention will be described using the drawings.

First Embodiment

A first embodiment of the invention will be described. The gamma ray irradiated from a Compton source is Compton-scattered by the pre-stage detector 51 and a scattered gamma ray 5A and a recoil electron 5B are generated. The scattered gamma ray 5A is detected by the post-stage detector 52. For each Compton scattering event, the following physical quantities such as energies and coordinates are obtained by the pre-stage data reader 53 and the post-stage data reader 54.

Compton scattering reaction point coordinate
Scattered gamma ray absorbing point coordinate
Scattered gamma ray energy
Recoil electron energy From these physical quantities, the data integration device 55 performs the calculation and thus Compton scattering angle
Scattered gamma ray direction are newly obtained. The image reconstruction device 56 performs the image reconstruction calculation using the two amounts.

Figure 6:
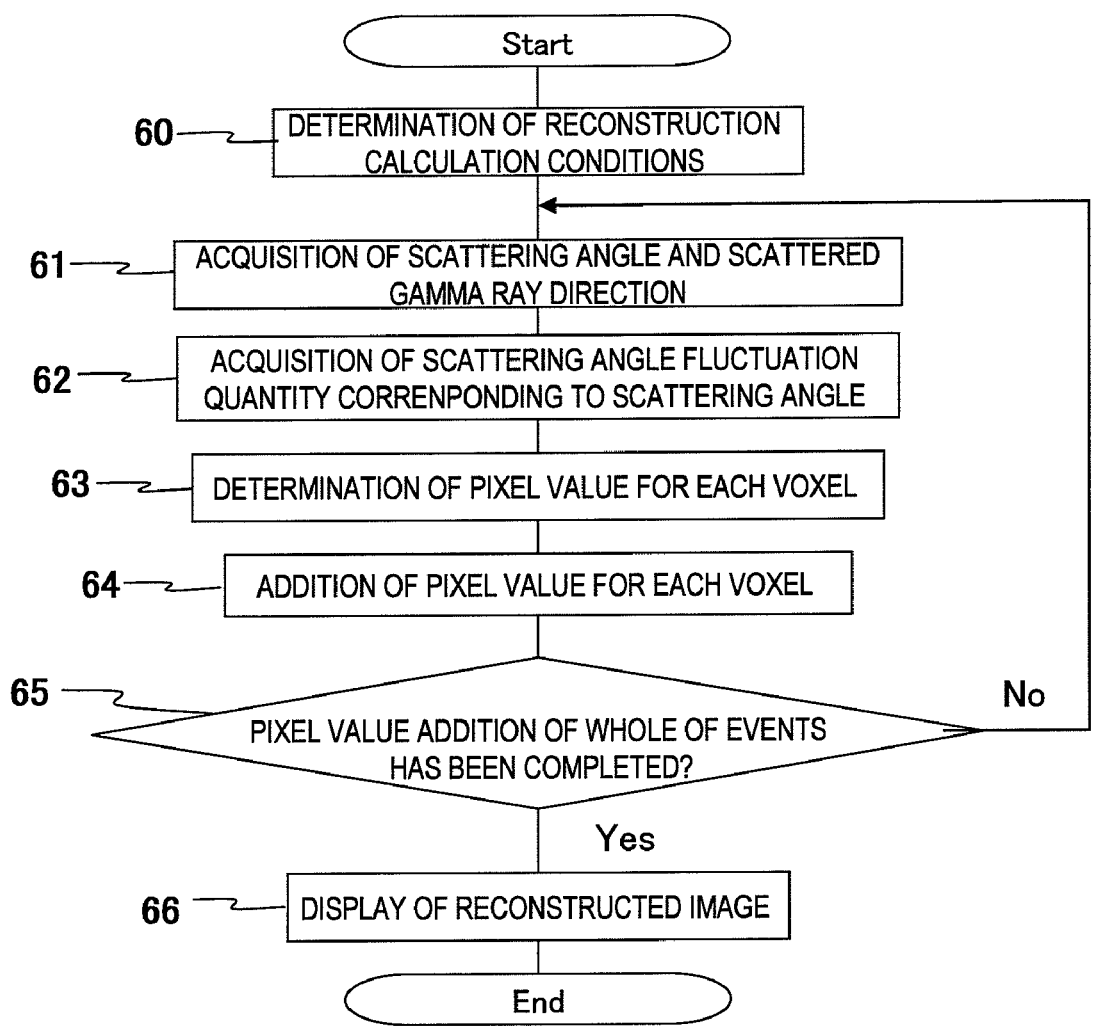
FIG. 6 is an image reconstruction calculation process flow common to first to third embodiments.

Herein, FIG. 6 shows a flowchart of the image reconstruction calculation. Steps of the flowchart will be described below.

[Step 60]

An operator operates the input device 58 to input conditions required for the image reconstruction calculation, such as the number of pixels of a reconstruction space, the size, or the number of the Compton scattering events used for the reconstruction calculation to the input device 58. Otherwise, the reconstruction calculation device 56 may allow the conditions to be inputted from the storage device 59 storing the pre-set reconstruction calculation conditions.

[Step 61]

The reconstruction calculation device 56 acquires a Compton scattering angle and a scattered gamma ray direction vector of a target Compton scattering event.

The reconstruction calculation device 56 acquires a scattering angle fluctuation amount suitable for the scattering angle of the target Compton scattering event from a database pre-stored in the storage device 59.

[Step 63]

The reconstruction calculation device 56 applies a pixel value to each voxel on the reconstruction space with a condition of (Formula 2).

{Expression 2}

$$F(\phi, \phi_0) = \begin{cases} \exp\left(-\frac{(\phi - \phi_0)^2}{2\Delta\phi(\phi_0)}\right) & \text{... if } |\phi - \phi_0| < \frac{1}{2}\Delta\phi(\phi_0) \\ 0 & \text{... else} \end{cases} \quad \text{(Formula 2)}$$

Where φ is a scattering angle when a target voxel is given as the ray source, φ0 is a measured scattering angle, and Δφ(φ0) is a scattering angle fluctuation quantity at the scattering angle φ0. In (Formula 2), a reconstruction function in accordance with Gauss distribution is defined, but another distribution function, such as Lorentz distribution (Formula 3), may be used.

{Expression 3}

$$F(\phi, \phi_0) = \begin{cases} \dfrac{[\Delta\phi(\phi_0)]^2}{\left\{(\phi-\phi_0)^2 + \dfrac{1}{4}[\Delta\phi(\phi_0)]^2\right\}} & \text{... if } |\phi-\phi_0| < \dfrac{1}{2}\Delta\phi(\phi_0) \\ 0 & \text{... else} \end{cases} \quad \text{(Formula 3)}$$

However, when it is found which distribution is used for the scattering angle fluctuation quantity, it is desirable to apply the known distribution function thereof.

[Step 64]

The reconstruction calculation device 56 adds a pixel value of each voxel obtained in Step 63 to a voxel value corresponding thereto on a reconstructed image.

The reconstruction calculation device 56 determines whether the pixel value adding process of the whole events as image reconstruction calculation targets has been completed. When the process has been completed, the process proceeds to Step 66, and when the process has not been completed, the process returns to Step 61 to continuously proceed.

[Step 66]

The reconstruction calculation device 56 outputs the reconstructed image to the display device 57. The display device 57 displays the reconstructed image.

According to this embodiment, a Compton camera device capable of obtaining a reconstructed image which is not affected by the difference in measurement accuracy can be provided. In addition, a particular advantage of the first embodiment is that the image reconstruction calculation considering a measurement error for each event is realized and resolution of the reconstructed image is improved. The first embodiment is particularly effective in cosmic ray source position determination or the like little requiring the high-accuracy measurement, in which the number of gamma rays incident to the camera is small.

Second Embodiment

Figure 7:
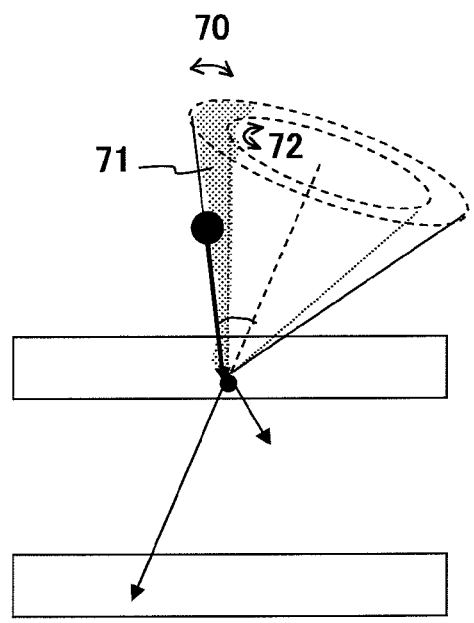
FIG. 7 is an explanatory diagram of a gamma ray existing area in the second embodiment.

A second embodiment of the invention will be described. This embodiment is an example of the embodiments considered when the pre-stage detector 51 obtains a recoil electron direction. For example, by using a gas chamber-type detector described in Patent Documents 1 and 2 as the pre-stage detector 51, the recoil electron direction can be acquired. Accordingly, it is possible to determine the direction of the gamma ray irradiated from the ray source by using the law of conservation of momentum from the scattered gamma ray direction vector and the recoil electron direction vector. Further, measurement errors of the directions of the scattered gamma ray and the recoil electron are considered and thus a part 71 of a cone surface having a thickness 70 as shown in FIG. 7 is formed. Herein, an error (fluctuation) 72 resulting from the direction determination accuracy is called a circumferential fluctuation (Δs) as shown in FIG. 7.

In this embodiment, a pixel value is acquired for each voxel and added as in the first embodiment. However, the calculation method of the pixel value of the voxel is different. In this embodiment, as in (Formula 4) (in the case of the Gauss distribution) or (Formula 5) (in the case of the Lorentz distribution), a pixel value of a target voxel is determined by using a reconstruction function employing the circumferential fluctuation.

{Expression 4}

$$F(\phi, s, \phi_0) = \begin{cases} \exp\left(-\dfrac{(\phi-\phi_0)^2}{2\Delta\phi(\phi_0)} - \dfrac{s^2}{2\Delta s}\right) & \text{... if } |\phi-\phi_0| < \dfrac{1}{2}\Delta\phi(\phi_0), |s| < \dfrac{1}{2}\Delta s \\ 0 & \text{... else} \end{cases} \quad \text{(Formula 4)}$$

{Expression 5}

$$F(\phi, s, \phi_0) = \begin{cases} \dfrac{[\Delta\phi(\phi_0)]^2}{\left\{(\phi-\phi_0)^2 + \dfrac{1}{4}[\Delta\phi(\phi_0)]^2\right\}} \dfrac{(\Delta s)^2}{\left\{s^2 + \dfrac{1}{4}(\Delta s)^2\right\}} & \text{... if } |\phi-\phi_0| < \dfrac{1}{2}\Delta\phi(\phi_0), |s| < \dfrac{1}{2}\Delta s \\ 0 & \text{... else} \end{cases} \quad \text{(Formula 5)}$$

Where s is an angle in a circumferential direction when the target voxel is given as the ray source and Δs is a circumferential fluctuation quantity. Needless to say, distribution functions other than (Formula 4) and (Formula 5) may be used.

According to this embodiment, a Compton camera device capable of obtaining a reconstructed image which is not affected by the difference in measurement accuracy can be provided. In addition, a particular advantage of the second embodiment is that noise existing in the background on the reconstructed image can be reduced because it is specified as a part of the cone surface having the thickness. Accordingly, this embodiment is particularly effective in the case in which a large number of gamma rays are incident on the camera from a plurality direction and the noise of the background easily increases, like a nuclear medicine field observing functional information such as metabolism and blood flow by the administration of radioactive agents.

Third Embodiment

A third embodiment of the invention will be described using FIG. 5. As shown in FIG. 5, when the scattering angle is small, the scattering angle fluctuation is also small, and as the scattering angle becomes larger, the scattering angle fluctuation also becomes larger. Accordingly, by increasing the weight of the event which is small in scattering angle and reducing the weight of the event which is large in scattering angle, the reconstruction functions (Formulas 2 to 5) are calculated and thus a reconstructed image which is not affected by the difference in measurement accuracy can be obtained. In addition, resolution of the reconstructed image is improved.

For example, in the reconstruction functions (Formulas 2 to 5), the scattering angle has a proportional relationship to the weighting factor. Regarding the kind of the weight, a linear shape may be simply used or a function reversing the left and the right of the scattering angle fluctuation curve of FIG. 5 may be used. Further, data no less than a certain scattering angle is large in measurement error and thus the weight of a part of which a predetermined measurement error is large may be set to 0.

Accordingly, for example, in the nuclear medicine field, in the case emphasizing a sensitivity, such as medical examination, the whole events may be used, and in the case requiring more accurate examination, the weighting may be performed to select only the events which are high in accuracy. A plurality of patterns of weighting functions may be provided to simultaneously display the respective reconstruction images on the display device 57.

Figure 8:
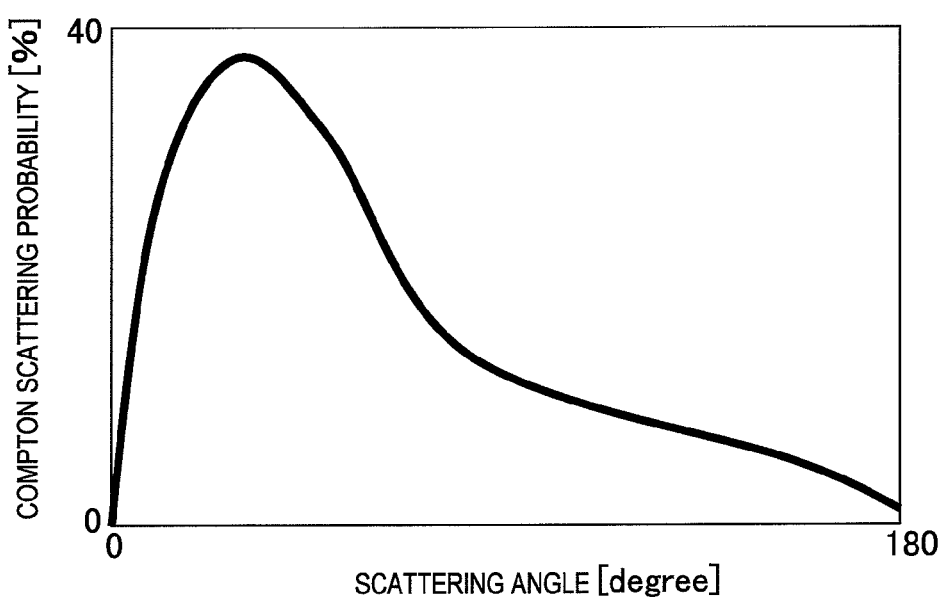
FIG. 8 is an example of a scattering angle and a Compton scattering event occurrence probability distribution.

As shown in FIG. 8, the probability of the occurrence of the Compton scattering event is different for each scattering angle. The outline of the graph of FIG. 8 changes in accordance with the energy of the incident gamma ray. When the energy of the incident gamma ray is high, the number of the events which are small in scattering angle increases. Thus, in this case, even when the weight of the event which is low in measurement accuracy, that is, the weight of the event which is large in scattering angle is set to 0 or a least value, the reduction of the sensitivity is suppressed to the minimum. The weighting function may be changed in accordance with the distribution of the event occurrence probability for each scattering angle.

According to this embodiment, a reconstructed image which is not affected by the difference in measurement accuracy can be obtained. A particular advantage of the third embodiment is that an image having higher resolution than in the case the image reconstruction is performed by the conventional Compton method can be obtained.

Figure 9:
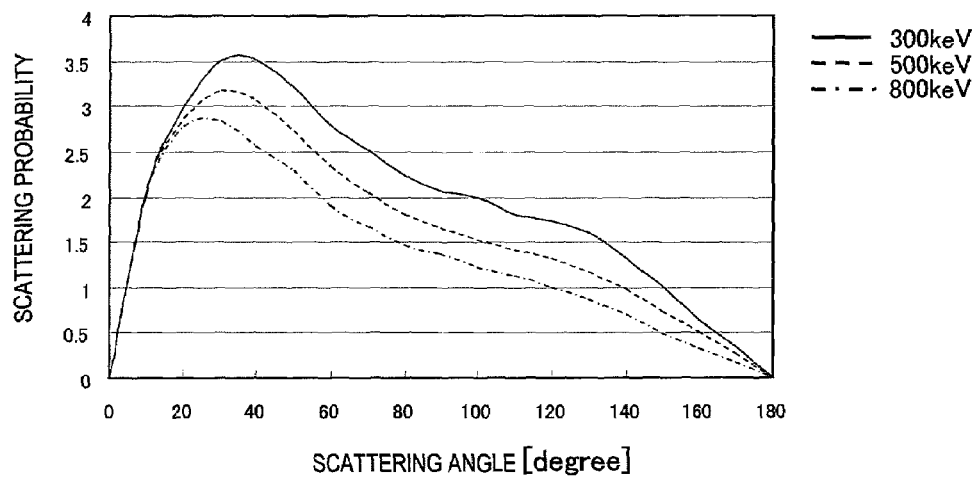
FIG. 9 is a diagram showing a relationship diagram of a scattering angle and a scattering probability.

When a relationship between the scattering angle fluctuation 30 and the scattering angle is represented by a graph, there is a tendency that the smaller the Compton scattering angle, the smaller the size of the scattering angle fluctuation, as shown in FIG. 4. FIG. 4 shows, as an example, the case where the incident gamma ray energy is 500 KeV. However, even in the case of the gamma ray having another energy, the tendency of the Compton scattering angle and the size of the scattering angle fluctuation does not change. In FIG. 9, a relationship between the probability of the Compton scattering and the scattering angle is shown. The graph shows that the smaller the scattering angle is, the more frequently the Compton scattering occurs. The characteristics of the Compton scattering obtained in FIGS. 4 and 9 are that the smaller the scattering angle is, the higher the Compton scattering probability is and the smaller the size of the scattering fluctuation is.

Herein, the angle ranging from a predetermined angle which is not used for the reconstruction process to an angle which is used for the reconstruction process is referred to as "optimal reconstruction angle" and the range ranging from the scattering angle of 0 degree to the "optimal reconstruction angle" is referred to as "optimal reconstruction angle range".

Fourth Embodiment

Figure 10:
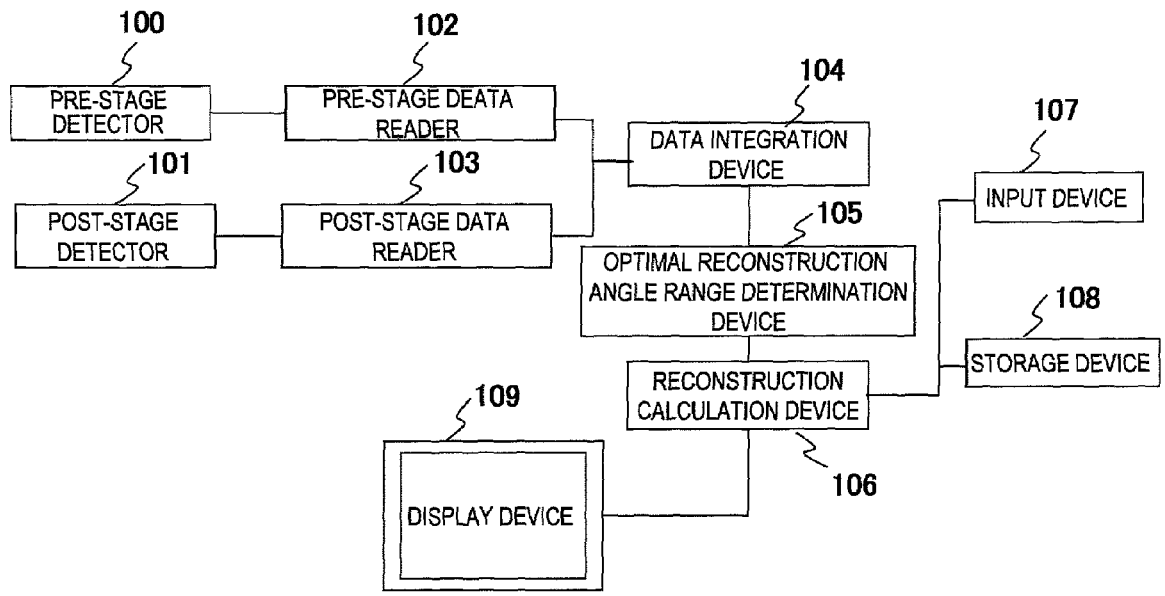
FIG. 10 is a diagram showing the configuration of a Compton camera device according to fourth to sixth embodiments.

Hereinafter, a fourth embodiment will be described in detail using the drawings. FIG. 10 shows an example of a gamma camera system according to the fourth embodiment. The gamma camera system takes a recoil electron and a scattered gamma ray causing the Compton scattering. Two detectors including a pre-stage detector and a post-stage detector represented by the reference numbers 100 and 101 of FIG. 10 are provided to take these signals.

Physical data such as an energy of the recoil electron and a Compton scattering reaction point coordinate detected by the pre-stage detector 100 is read by a pre-stage data reader. The post-stage detector 101 detects a scattered gamma ray energy, a scattered gamma ray absorbing position coordinate and the like and these physical quantities are read by a post-stage data reader 103.

A data integration device 104 for integrating the data obtained by the readers 102 and 103 and newly calculating physical quantities such as a scattered gamma ray direction and a Compton scattering angle is connected to the readers. An image reconstruction calculation device 106 for acquiring information such as the scattering angle and the Compton scattering reaction point coordinate from the data integration device 104 and performing image reconstruction calculation of a ray source, a display device 109 for displaying a reconstructed image, an optimal reconstruction angle range determination device 105 for instructing the image reconstruction calculation device 106 on an optimal Compton scattering angle range for the reconstruction process, an input device 107 such as keyboard or mouse for inputting reconstruction conditions, and a storage device 108 for storing pre-set reconstruction calculation conditions, measurement error information of the evaluated camera and the like, and if necessary, providing the information to the reconstruction calculation device 106 are provided. Since the optimal reconstruction angle range determination device 105 shows characteristics of the fourth embodiment, the device will be described below.

In this embodiment, the optimal reconstruction angle range determination device 105 calculates the optimal reconstruction angle and the information is provided to a reconstruction calculation device 100.

Figure 11:
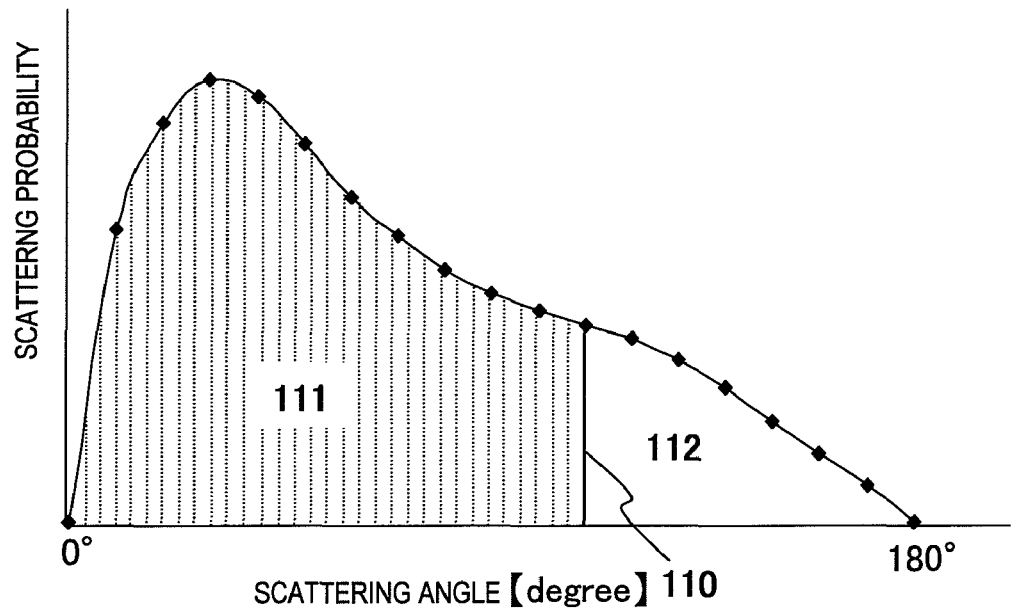
FIG. 11 is a graph showing a Compton scattering angle and the probability of the occurrence thereof at an incident gamma ray energy of 500 KeV.

The graph of FIG. 11 is a graph of a Compton scattering angle and the probability of the occurrence thereof at an incident gamma energy of 500 KeV and is a curve obtained by a complicated formula referred to as the Klein-Nishina formula for the amplification of a photon energy caused by the Compton scattering. An optimal reconstruction angle 110 is determined from an area of a region surrounded by the graph and the Y axis.

Figure 12:
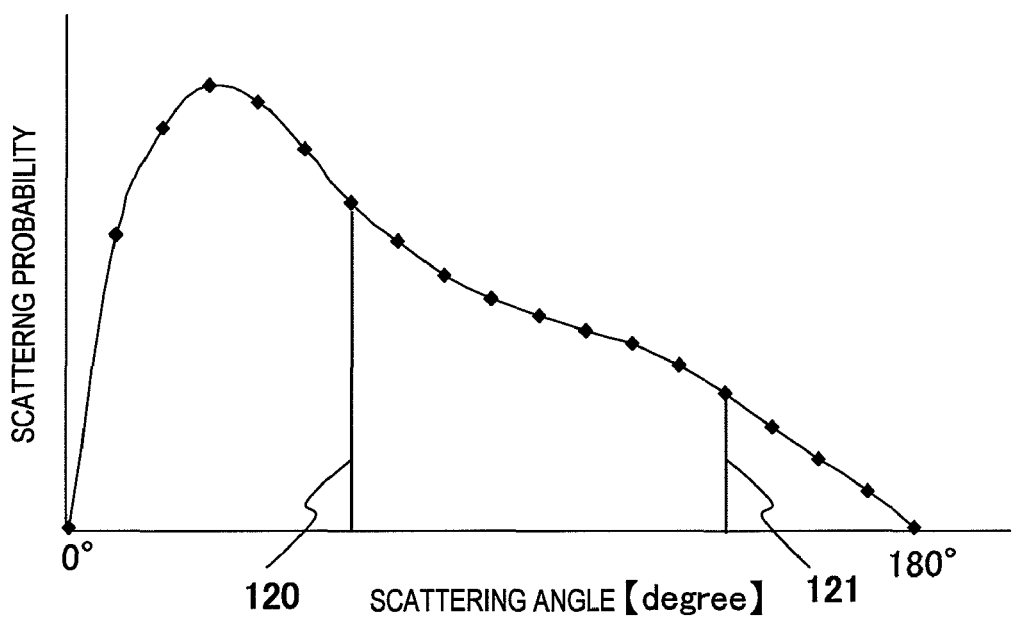
FIG. 12 is a diagram explaining an example of the setting of a scattering probability with respect to a Compton scattering angle.

For example, the optimal reconstruction angle 110 is determined so that an area ratio of a shaded part 111 to a region 112 of FIG. 11 is 60:40 (hereinafter, optimal area ratio). The calculation of the areas can be performed by a general integral formula. Other than the method of calculating the areas by the integral formula, an area calculation method using a probability distribution such as a Monte Carlo method may be used. The setting of the optimal reconstruction angle determined by the area ratio changes. For example, it is possible to set the optimal scattering angle on the angle side in which the scattering angle is extremely small with the area ratio of 30:70 (see FIG. 12 and the reference number 120). On the other hand, it is possible to set an optimal reconstruction angle 121 on the angle side in which the scattering angle is large with the area ratio of 90:10.

Accordingly, in the nuclear medicine field, in the case emphasizing a sensitivity, such as medical examination, the reconstruction process is performed with the wide optimal reconstruction angle range like the reference number 121, and in the case requiring more accurate examination, the acquisition of a reconstructed image with the reconstruction angle range determined by the optimal reconstruction angle represented by the reference number 120 is effective in usage in clinical practice and thus the optimal reconstruction angle is changeably set in this embodiment.

In the above description, the case where a single incident gamma ray energy is provided has been described. The gamma camera device used in clinical practice is designed for a gamma ray source having a variety of energies. This is because a variety of nuclides are administered into a troubled area of a human body to obtain an image of a position on which the nuclides are accumulated. Examples thereof are bone scintigraphy employing 99 mTc as a nuclide and the acquisition of a glucose metabolism image employing 18F-FDG as a nuclide.

The former is used for early detection of a bone tumor and the like and the latter is used for detection of primary/metastatic malignancies and the like. The energy of 99 mTc is 141 KeV and the energy of 18F-FDG is 511 KeV. As shown in FIG. 9, the shape and the like of the graph of the Compton scattering angle and the Compton scattering probability (hereinafter, Compton scattering probability distribution curve) largely change in accordance with the energy of the incident gamma ray. Thus, in order to improve resolution of a reconstructed image, it is required to set the optimal reconstruction angle by a variety of energies. As described above, as shown in FIG. 11, the optimal reconstruction angle can be obtained from the Compton scattering probability distribution curve obtained by the Klein-Nishina formula for each energy of a nuclide by using the area ratio.

Figure 13:
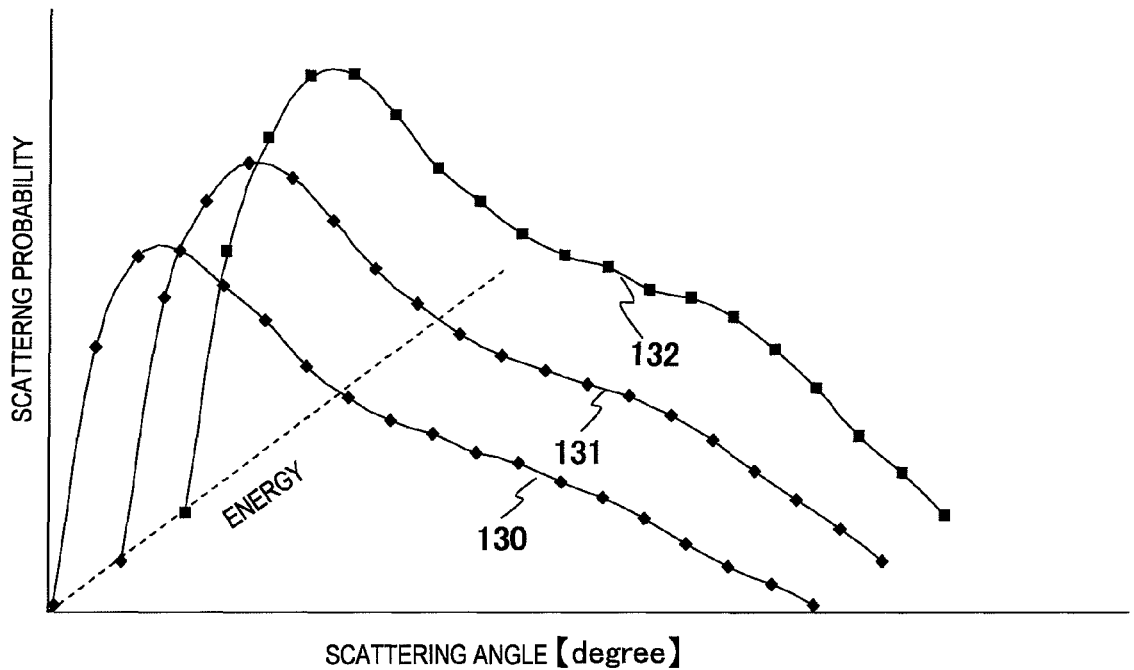
FIG. 13 is a diagram showing a Compton scattering probability distribution curve at a typical energy.

In this embodiment, first, as shown in FIG. 13, the Compton scattering probability distribution curve at a typical energy is obtained. In the example of FIG. 13, the Compton scattering probability distribution curves at the reference number 130 of 800 KeV, the reference number 131 of 500 KeV, and the reference number 132 of 300 KeV are shown. From the three curves, a regression curved surface is obtained as represented by the reference number 140 of FIG. 14. The regression curved surface is a general approximation method extending an approximate curve of a least-square method to a curved surface equation. In this embodiment, the regression curved surface of the three curves is used, but the three curves are used as an example and the number of the curves is not limited. By the regression curved surface equation, the Compton scattering probability distribution curve at an arbitrary energy can be approximated.

Figure 14:
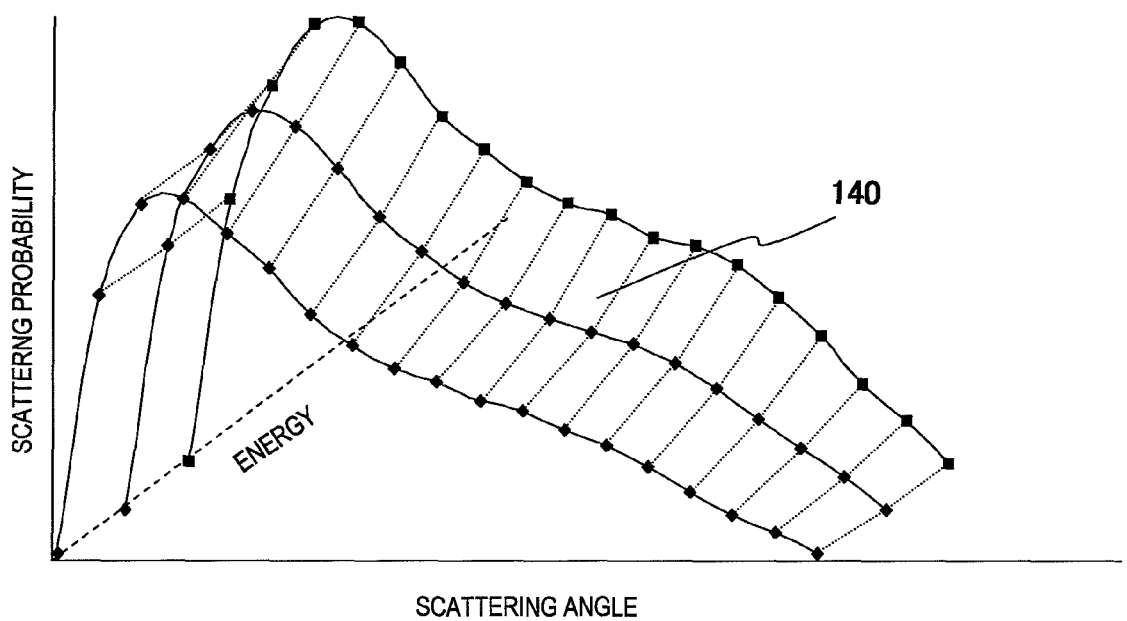
FIG. 14 is a diagram explaining an example of the calculation of a regression curve for approximating a Compton scattering probability distribution curve at an arbitrary energy.

In FIG. 14, the curved surface equation at the energy of 300 KeV to 800 KeV is shown. The regression curved surface equation also exists outside the above range. From the obtained curved surface equation, a general formula (Compton scattering probability distribution curve) for only the energy required can be represented by an easy formula and this formula is a far easier formula than the Klein-Nishina formula. Accordingly, from the formula, it is possible to easily obtain the optimal reconstruction angle depending on the area ratio obtained using the integral formula or the Monte Carlo method and a Compton camera device effective in clinical practice and capable of handling a variety of nuclides having an arbitrary incident energy can be realized.

Fifth Embodiment

In a fifth embodiment, by using FIG. 15, a description will be made for a determination method of the optimal reconstruction angle range and the optimal reconstruction angle further extending the method described in the fourth embodiment.

Figure 15:
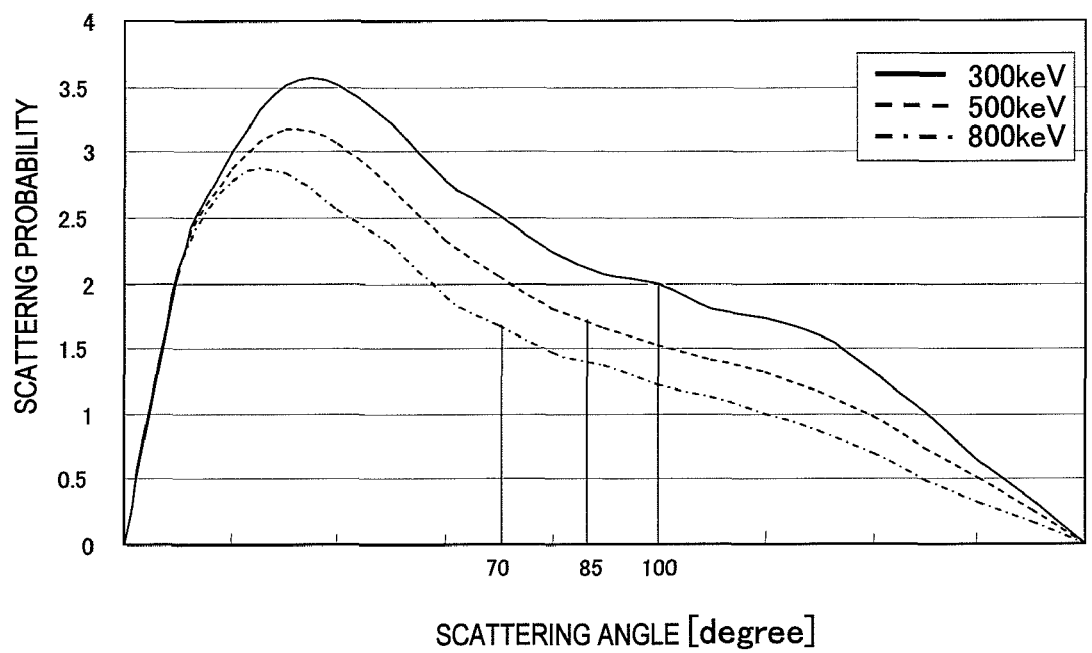
FIG. 15 is a diagram explaining an example of the calculation of an optimal scattering angle at three kinds of energies.

FIG. 15 shows the Compton scattering probability distribution curves at 300, 500 and 800 KeV. In this embodiment, the optimal reconstruction angle at an arbitrary energy (herein, three kinds of 300, 500 and 800 KeV) is calculated in advance. For the calculation, the method described in the first embodiment may be used and it is preferable to determine the optimal scattering angle so that the optimal area ratio described above is 60:40. In FIG. 15, the optimal scattering angles obtained at the three kinds of energies are shown. FIG. 15 schematically shows the optimal reconstruction angle at each energy. That is, they are values for the description calculated without the acquisition of the accurate optimal area ratio.

Figure 16:
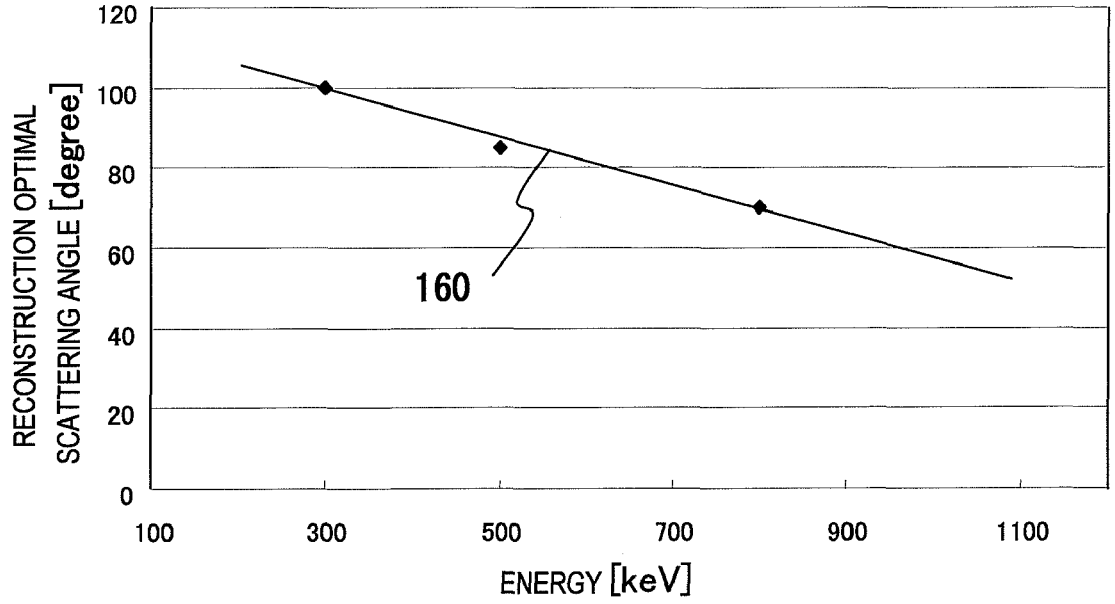
FIG. 16 is a diagram explaining an example of the calculation of an optimal reconstruction angle at an arbitrary energy using a regression curve.

The optimal reconstruction angle is 100° at 300 KeV, the optimal reconstruction angle is 85° at 500 KeV, and the optimal reconstruction angle is 70° at 800 KeV. FIG. 16 shows the above values plotted on the graph. They are plotted with a horizontal axis representing the incident gamma ray energy and a vertical axis representing the optimal reconstruction angle. A regression line 160 drawn on the basis of the plotted values is shown in the drawing. When using the regression line, it is possible to easily calculate the optimal reconstruction angle at an arbitrary energy (in case of the optimal area ratio of 60:40). In FIG. 16, the description is made using the regression line. However, when the increase of the fitting accuracy is required, a regression curve may be calculated by using a quadratic function or the like to set the optimal reconstruction angle.

As described above, in this embodiment, when the optimal area ratio is fixed, the optimal reconstruction angle is calculated at an arbitrary energy by using the regression line. As compared with the fourth embodiment, it is advantageous in ease of the calculation.

Although the optimal area ratio is fixed, the optimal reconstruction angle is calculated so as to preliminarily adjust the optimal area ratio to, for example, 80:20, and in this manner, it is possible to handle a variety of area ratios. At such a variety of area ratios, the regression line or the regression curve of the optimal reconstruction angle and the energy can be obtained, and from them, the regression curved surface equation or the regression plane equation also can be calculated. In addition, from them, the optimal reconstruction angle at an arbitrary energy and an arbitrary optimal area ratio also can be calculated.

Sixth Embodiment

In a sixth embodiment, a description will be made for a gamma camera device according to the invention handling a subject into which, for example, a plurality of nuclides which are different from each other in incident energy are administered. For example, in the clinical practice, it is quite possible that two nuclides 99 mTc and 18F-FDG are administered. When the optimal reconstruction angle for 99 mTc put before 18F-FDG is determined and the reconstruction process is performed, it may bring disadvantages in the clinical practice, such as the reduction of resolution of a reconstructed image of a troubled area on which 18F-FDG is accumulated. In this embodiment, the disadvantages are solved as follows. For example, when the optimal area ratio is 60:40, the optimal reconstruction angle for 99 mTc is assumed to be 60° and the optimal reconstruction angle for 18F-FDG is assumed to be 75°.

In this embodiment, the reconstruction process is performed for each nuclide by using the optimal reconstruction angle of each nuclide. That is, the reconstruction process is performed two times. In addition, two reconstructed images obtained by the two reconstruction processes are fused and displayed as one image. The fusing method is referred to as the image fusion or the like and a known method frequently used in PET-CT is used. By using the method, the reduction in any one of resolutions of images of agent accumulation places different depending on the nuclide (when two nuclides are administered) does not occur. Herein, the case where the two nuclides are administered has been described. However, this embodiment is effective even when two or more nuclides are administered and it is preferable to perform the reconstruction process by using the optimal reconstruction angle for each nuclide.

It is preferable to perform the image fusion display of a plurality of the nuclides as needed in diagnosis and the like and it is possible to independently display a plurality of the images obtained for each nuclide.

The invention claimed is:

1. A Compton camera device comprising:
    a pre-stage detector for directly detecting a quantum ray including a cosmic ray and a gamma ray;
    a post-stage detector for detecting the quantum ray incident to the pre-stage detector and scattered by a Compton scattering phenomenon;
    image reconstruction means for reconstructing the distribution of the quantum ray detected by the pre-stage detector and the post-stage detector as image information; and
    display means for displaying the image information subjected to the image reconstruction,
    the device further comprising:
    first means for reading coordinate data of a scattering point of the quantum ray detected by the pre-stage detector for each Compton scattering event;
    second means for reading coordinate data of a reaching point of the Compton-scattered quantum ray detected by the post-stage detector for each Compton scattering event; and
    third means for calculating a measurement accuracy of the scattered quantum ray by the first and second means for each Compton scattering event, calculating a statistical quantity of the quantum ray for each calculated measurement accuracy, and outputting the calculated statistical quantity to the image reconstruction means.

2. The Compton camera device according to claim 1, wherein the measurement accuracy of the scattered quantum ray of the third means is dependent on a Compton scattering angle.

3. The Compton camera device according to claim 1, wherein the third means calculates a direction of a recoil electron generated for each Compton scattering event.

4. The Compton camera device according to claim 1, wherein the third means calculates the weighting of the events for each calculated measurement accuracy.

5. The Compton camera device according to claim 1, wherein the third means calculates an optimal reconstruction angle range according to an incident energy of the quantum ray.

6. The Compton camera device according to claim 5, wherein the third means calculates a Compton scattering probability distribution curve and a Compton scattering angle at the incident energy of the quantum ray and calculates an optimal reconstruction angle range which is used for the reconstruction by an area of a region surrounded by the calculated Compton scattering probability distribution curve and an axis of the scattering angle.

7. The Compton camera device according to claim 5, wherein the third means calculates a Compton scattering probability distribution curve at a plurality of incident energies of the quantum rays, calculates a regression curved surface of the Compton scattering probability and the scattering angle at an arbitrary incident energy from the calculated Compton scattering probability distribution curves, and calculates an optimal reconstruction angle range at an arbitrary incident energy from the regression curved surface.

8. The Compton camera device according to claim 5, wherein the third means calculates a Compton scattering probability distribution curve at a plurality of incident energies of the quantum rays, preliminarily obtains an optimal reconstruction angle at the calculated plurality of incident energies, obtains a regression curve from the optimal reconstruction angle and the incident energies, and sets an optimal reconstruction angle range at an arbitrary incident energy by using the regression curve.

9. The Compton camera device according to claim 1, wherein the image reconstruction means performs the reconstruction process for each incident energy of the quantum ray and creates a synthesized image by using the reconstructed images.

10. A Compton camera device comprising:
    a pre-stage detector for directly detecting a gamma ray emitted from an agent, the agent containing a radioisotope being administered into a subject and accumulated in a predetermined viscera or organ;
    a post-stage detector for detecting the gamma ray incident on the pre-stage detector and scattered by a Compton scattering phenomenon;
    image reconstruction means for subjecting image information on the distribution of the gamma ray detected by the pre-stage detector and the post-stage detector to image reconstruction; and
    display means for displaying the image information subjected to the image reconstruction,
    the device further comprising:
    first means for reading coordinate data of a scattering point of the quantum ray detected by the pre-stage detector for each Compton scattering event;
    second means for reading coordinate data of a reaching point of the Compton-scattered quantum ray detected by the post-stage detector for each Compton scattering event; and
    third means for calculating a measurement accuracy of the scattered quantum ray by the first and second means for each Compton scattering event, calculating a statistical quantity of the quantum ray for each calculated measurement accuracy, and outputting the calculated statistical quantity to the image reconstruction means.

* * * * *